(12) United States Patent
Offenhäusser et al.

(10) Patent No.: US 7,632,670 B2
(45) Date of Patent: Dec. 15, 2009

(54) FET SENSOR WITH SPECIALLY CONFIGURED GATE ELECTRODE FOR THE HIGHLY SENSITIVE DETECTION OF ANALYTES

(75) Inventors: Andreas Offenhäusser, Eynatten (BE); Margarete Odenthal, Köln (DE); Michael Goryll, Aachen (DE); Jürgen Moers, Viersen (DE); Hans Lüth, Aachen (DE)

(73) Assignee: Forschungszentrum Julich GmbH, Julich (DE)

( * ) Notice: Subject to any disclaimer, the term of this patent is extended or adjusted under 35 U.S.C. 154(b) by 324 days.

(21) Appl. No.: 10/499,751

(22) PCT Filed: Dec. 14, 2002

(86) PCT No.: PCT/DE02/04594

§ 371 (c)(1),
(2), (4) Date: Jun. 18, 2004

(87) PCT Pub. No.: WO03/056322

PCT Pub. Date: Jul. 10, 2003

(65) Prior Publication Data

US 2005/0040483 A1    Feb. 24, 2005

(30) Foreign Application Priority Data

Dec. 21, 2001    (DE) ................................ 101 63 557

(51) Int. Cl.
*C12M 1/34*    (2006.01)
(52) U.S. Cl. ................. 435/287.1; 435/285.2; 436/518; 436/524
(58) Field of Classification Search ................... 204/461
See application file for complete search history.

(56) References Cited

U.S. PATENT DOCUMENTS 4,020,830 A * 5/1977 Johnson et al. ............. 600/348
4,778,769 A    10/1988 Forrest et al.
4,881,109 A * 11/1989 Ogawa ....................... 257/253
5,384,028 A    1/1995 Ito (Continued)

FOREIGN PATENT DOCUMENTS

| DE | 42 32 532 | 4/1994 |
| DE | 48 08 081 | 9/1994 |
| JP | 62237347 | 10/1987 |
| JP | 09082958 | 3/1997 |
| WO | WO 01/64945 | 9/2001 |

OTHER PUBLICATIONS

Electrostatically Protected Ion Sensitive Field . . . R. Smith et al. (Sensors & Actuators, May 1984).
A Novel Self-Aligned T-Shaped Gate Process . . . by Horng-Chih Lin et al. (IEEE Jan. 1998).
A Process for the Combined Fabrication of Ion Sensors . . . by L. Bousse et al. (IEEE Jan. 1988).

*Primary Examiner*—N C Yang
(74) *Attorney, Agent, or Firm*—Andrew Wilford

(57) ABSTRACT

Disclosed is a sensor comprising a substrate, a source contact region, a drain contact region, and the gate oxide of a transistor. A gate electrode is disposed between the gate oxide and a detection electrode made of a nonconducting material. The contact area $A_{sens}$ between the gate electrode and the detection electrode is larger than the contact area $A_{gate}$ between the gate electrode and the gate oxide, whereby the receptor can be immobilized on the surface of the detection electrode in a technically simple manner while the small contact area $A_{gate}$ between the gate electrode and the transistor provides for high sensitivity for detecting the analyte. According to the inventive method for detecting at least one analyte, at least one analyte is brought into contact with a receptor immobilized at the detection electrode so as to modify the electrical charge at the surface of the detection electrode. The analyte is detected by detecting the modified voltage in the transistor.

10 Claims, 1 Drawing Sheet

U.S. PATENT DOCUMENTS 6,077,733 A * 6/2000 Chen et al. .................. 438/182
6,284,613 B1 9/2001 Subrahmanyam et al.
2001/0033027 A1 * 10/2001 Akram et al. ............... 257/763
2002/0006632 A1 * 1/2002 Ponnampalam et al. .... 435/7.92

* cited by examiner

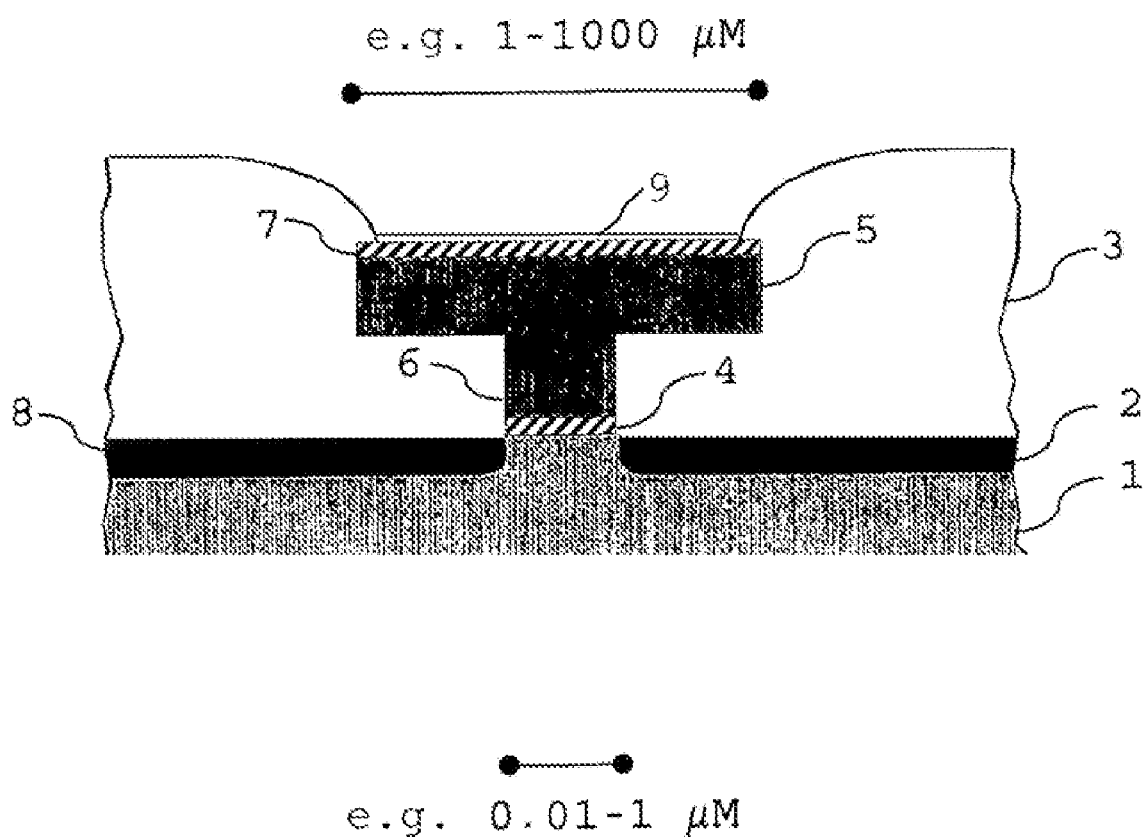

FET SENSOR WITH SPECIALLY CONFIGURED GATE ELECTRODE FOR THE HIGHLY SENSITIVE DETECTION OF ANALYTES

CROSS REFERENCE TO RELATED APPLICATIONS

This application is the US national phase of PCT application PCT/DE02/04594, filed 14 Dec. 2002, published 10 Jul. 2003 as WO 2003/056322, and claiming the priority of German patent application 10163557.5 itself filed 21 Dec. 2001, whose entire disclosures are herewith incorporated by reference.

FIELD OF THE INVENTION

The invention relates to a transistor-based sensor with a specially formed gate electrode for the highly sensitive detection of analytes.

FIELD OF THE INVENTION

In recent years sensors have been developed utilizing silicon-based microelectronic components which have become of significant importance since the sensor and its evaluating electronics can be integrated monolithically on a chip utilizing silicon-CMOS technology. By combining a microelectronic component and a sensor, the matching of the sensitivity of the component and the sensitivity of the sensor is always fraught with problems. From the electronic point of view the sensor which best serves for the component is the MOSFET. This kind of component has over the last two decades been in continuous development and of considerable significance in microelectronics. The critical component dimensions and the electronic characteristics have been continuously reduced and improved, respectively. Because of the reduction of the dimensions, the transistors have not only been made faster acting but also more sensitive. At the start of the 90s, the dimensions were reduced below the previous limits of 1 micrometer. Present day components have standard channel lengths of 180 nanometers (nm).

This dimension is shortly expected, in production quantities, to be reduced to 130 nm.

In the International Technology Roadmap for Semiconductors (see the cited website) the component dimensions and electronic characteristics of MOSFETs have been predicted through the years of 2015. Laboratory specimens for future applications and components, however, have been prepared even at this stage.

Because of this scaling, apart from technical problems, certain physical problems arise such that without certain steps, the electronic characteristics can be degraded. The properties of the transistors cannot simply be scaled to match the size since so-called short channel effects arise. These effects which characterize the extremely small components must be avoided by a modified configuration of the layout.

A possible solution to the problem can be the known fully depleted silicon-on-insulator (FD-SOI) transistor or the double-gate (DG) transistor. In the fully depleted silicon-on-insulator transistors (FD-SOI), there is a layer of several nanometers in thickness forming a current-conducting layer on a buried oxide layer. In the case of a double-gate transistor (DG-MOSFET), the current conducting layer is controlled from both sides by respective control electrodes. This advantageously results in a decrease in the spatial requirements per component which is significant in industrial applications since more units can be obtained for a given price and thus the unit cost can be reduced. As far as the component properties are concerned, the smaller dimensions mean higher sensitivity in the sense that smaller input signals the same level of output signals can be achieved. This characteristic is generally of great significance for the use of such systems in sensor or analytic technology.

For biomedicinal applications, sensors have been divided to date into substantially the following groups. Enzymatic biosensors (for example glucose and urea sensors), affinity biosensors (for example immunosensors, DNA sensors), whole cell biosensors (microbe sensors, tissue sensors, nerve cell sensors). For signal conversion, usually the following structures are thus used: impedance structures, acoustic-wave structures, calorimetric sensors, electrochemical cells, optical sensors as well as sensors based upon semiconductors.

Apart from light-addressable semiconductor structures (LAPS) and capacitive sensors, from Bergveld (Bergveld, P., 1970. Development of an ion-sensitive solid-state device for neurophysiological measurements. IEEE Trans. Biomed. Eng. BME-17, 70-71), it is known to use transistor structures which, by contrast with the classical field-effect transistors (MOSFETS), have no metallic gates. Thus, for example, with receptor-based sensors, the surface of the gate oxide material can be sensitive to a corresponding target substance. If a corresponding target substance is found in the solution, it can bind to the correspondingly immobilized receptor substance which can increase the electric charge on the sensor. As a consequence, there is a change of the charge in the channel of the component which gives rise to a measurable change in its characteristics. Apart from several drawbacks which are a consequence mainly of effects at the electrolyte/component interface, there is a significant drawback in the indicated structure in that the fabrication of the component used cannot be carried out by present day standard CMOS processes.

There is a need for sensors which are CMOS compatible so that signal processing as well as further sensors, for example for temperature measurements, can all be provided on a single chip. The compatibility for CMOS processing has thereby previously been enhanced in that with CMOS technology, it is customary to use a polysilicon gate. From Bousse et al (Bousse, L., Shott, J., Meindl, J. D. 1988. A process for the combined fabrication of ion sensors and CMOS circuits. IEEE Electron Device Lett. 9, 44-46), it is known in this connection, to operate the polysilicon gate so that it is electrically floating. By electrically floating we mean that its potential is determined by the charge and is not fixed.

From Smith et al (Smith, R., Huber, R. J., Janata, J., 1984. Electrostatically protected ion sensitive field effect transistors. Sensors and Actuators, 5, 127-136), it is known to control a polysilicon gate by the use of MOSFET switching. In this case, a transistor is formed in which polysilicon is applied as the material for the gate electrode. On the gate electrode there is provided a platinum layer whose area is selected to be greater than that of the gate electrode in order to minimize the current density at the transition from the electrolyte to the metal.

In biomedicine and diagnostics, the detection of the smallest molecular concentrations can be of considerable importance. Thus, for example, in DNA analysis there is a requirement for a detection process which is so sensitive that the DNA multiplication steps involving the polymerase chain reaction (PCR) will become superfluous. These steps are disadvantageously labor-intensive and expensive. As a consequence, it is necessary to develop sensors which can detect even a few molecules of an analyte. It is especially interesting in molecular diagnostics, for example, from a few cells (for example, after a biopsy) to obtain a genetic fingerprint on a DNA basis. The genetic material is dissolved from the cells and a small amount of the sample is analyzed. In addition to the known DNA chips, there is a need for chips which are effective in the proteomic range.

One possibility for the detection of small quantities of sample material resides in the use of very small or surfaces for the detection electrode with correspondingly more sensitive sensors. For this purpose a receptor for the analyte is locally applied to a very small area or surface of the detection electrode. The local immobilization of the receptor on such a small area is, however, disadvantageous since it is releasable only with high labor cost and high costs otherwise.

OBJECT OF THE INVENTION

The object of the invention is thus to provide a sensor which does not have the indicated drawbacks of the state of the art. Especially, the sensor should be compatible with the CMOS standard processes and simultaneously should be capable of detecting at least one analyte by means of its conversion by or its binding to a receptor.

SUMMARY OF THE INVENTION

The object is attained with a sensor where between a detection electrode of an electrically insulating material and a gate oxide forming a dielectri of a transistor, a gate electrode is disposed. The gate electrode has a large contact area $A_{sens}$ for the detection electrode and a small contact area $A_{gate}$ at the gate oxide of the submicrometer transistor or nanotransistor. The receptor for binding or reaction with the analyte is immobilized on the surface of the detection electrode. The term "analyte" includes especially biomolecules like nucleic acids (RNA, DNA), antigens and substrates of immobilized enzymes. The term "receptor" thus encompasses all molecules which combine such analytes or reacts with them whereby the analyte can be detected.

Because of the greater area of the detection electrode it is possible to ensure that the receptor can be immobilized in a technologically simple manner on the detection electrode.

Because of the smaller contact area $A_{gate}$ of the gate electrode of the transistor, simultaneously a high detection sensitivity for the analyte is obtained since the sensor according to the invention through the use of the insulating material always involves a series circuit of two condensers or capacitors. The first condenser or capacitor is between the receptor on the dielectric detection electrode and the large-area face of the conductive gate electrode material. The second condenser or capacitor is provided between small-area face of the gate electrode material and the silicon substrate spaced from this small-area face by the dielectric gate oxide.

The larger area of the detection electrode can be formed by a correspondingly large contact surface $A_{sens}$ of the gate electrode. Because of the insulating properties of the detection electrode, this detection electrode is electrically separated from the gate electrode. Its capacity $C_{sens}$ is given by equation (1) which has been derived for the capacity of a plate condenser:

$$C = \frac{\varepsilon_o \cdot \varepsilon_r \cdot A}{d} \quad (1)$$

In the formula (1) A is the plate area; d is the plate spacing $\varepsilon_o$ is the electrical field constant; and $\varepsilon_r$ is the relative dielectric constant of the dielectric.

The capacitance of the gate electrode as the control electrode of the transistor is correspondingly less because of the clearly smaller contract area $A_{gate}$ of the gate electrode at the transistor under the supposition that the thicknesses of the insulating layers $d_{sens}$ and $d_{gate}$ do not differ from one another or differ only insubstantially from one another.

The capacitance of the gate electrode can be approximated as well from the aforementioned formula. The gate capacitance is, because of the dimensioning of the submicrometer or nanotransistor used, significantly smaller than that of the detection electrode. Since the relationship between the capacitance and the voltage of the condenser is given by the relationship $$C = \frac{dQ}{dU} \quad (2)$$

the above-described arrangement defines the following relationship between the two capacitors:

$$\frac{C_{sens}}{C_{gate}} = \frac{dQ_{sens}}{dQ_{gate}} \cdot \frac{dU_{gate}}{dU_{sens}} = \frac{dU_{gate}}{dU_{sens}} \quad (3)$$

which results in an increase in the voltage at the gate electrode since $dQ_{sens}$ equals $dQ_{gate}$, i.e. identical charges are picked up by both capacitances. In combination with a submicrometer transistor or nanotransistor this ensures an improved sensitivity. As a result, the use of a sensor with the above-mentioned dimensions for the gate electrode means that even a few molecules of an analyte can be detectable on the surface of the detection electrode as long as there is a change in the charge at the detection electrode resulting from the receptor by binding to or reacting with the analyte. For the detection, initially the analyte must be brought into contract with the immobilized receptor on the detection electrode. This results in a change in the electrical charge on the surface of the detection electrode. The charge is transferred according to the invention through the series circuit of the two condensers to the transistor whereby the charge density is increased in the direction of the transistor (see equation 3) because of the dimensioning of the gate electrode at the contact area with the detection electrode $A_{sens}$ and at the gate oxide $A_{gate}$. The concentration of the detected analyte is determined by the measurement of the current change.

An advantage of this concept is that the linking of a large detection area with a submicrometer transistor or nanotransistor is largely independent of the particular nanotransistor concept which may be used. The concept is thus compatible with nanotransistors which have previously been described in the literature. It is especially compatible with nano-MOS-transistors.

Preferably the ratio of the areas $A_{gate}:A_{sens}$ is 1:10 to 1:500, 000

To provide the first condenser or capacitor, the detection electrode is composed of an insulating material. The detection electrode can be composed of $SiO_2$. $SiO_2$ is a good insulator. The material can be applied in very thin layers. The smallest charge changes on the surface of the detection electrode as a result of binding an analyte to an immobilized receptor molecule can thus be transferred with high sensitivity via the first condenser in the direction of the transistor. Furthermore, the invention allows biomolecules like for example nucleic acids, antibodies and enzymes to be used as receptors by processes which have been developed in the state of the art in silane chemistry for immobilizing them on $SiO_2$ Apart from $SiO_2$ as a material for the detection electrode, also $Ta_2O_5$, $Al_2O_3$ or $Si_3N_4$ have been found to be especially suitable. These materials are also good insulators. They are characterized moreover especially as pH sensitive materials for the detection of substrates as analytes which in the course of a reaction with an immobilized enzyme for example with dehydrogenase, can be reacted. As a result there is a detectable local charge in the pH value at the detection electrode which detects the analyte.

In an advantageous embodiment of the invention a highly conductive polysilicon is used as the gate electrode material. This has the advantageous effect that the gate electrode material is capacitatively coupled to the detection electrode. This ensues a good signal transmission from the detection electrode to the gate electrode. It will be self-understood that the material of the gate electrode is not limited to polysilicon. Rather, all materials of good conductivity which have been used as gates can be used for the gate electrode.

The gate electrode and the detection electrode can be connected with one another by one more layers. In the region between the gate electrode and the detection electrode a silicide layer can be arranged as the surface of the sole electrode. The silicide layer can for example be produced by the sputtering of tungsten on the polysilicon and subsequently heat treating it. Following the sputtering deposition of titanium, a layer of titanium silicide can be formed as the surface of the gate electrode. Advantageously, the mentioned silicides are very good conductors. They prevent an ion flow to the transistor and increase the durability of the transistor.

In an especially advantageous feature of the invention, a layer sequence is provided of polysilicon, tungsten silicide and $SiO_2$ to form a first condenser. The layer of tungsten silicide is disposed on the polysilicon and forms the surface of the gate electrode. Such a layer sequence with $SiO_2$ as the insulating layer for the detection electrode gives rise to the capacitative coupling of the gate electrode to the detection electrode.

The corresponding materials for the gate electrode are those which have already been found to be useful for the fabrication of transistors in the submicrometer range or nanometer range and do not have any detrimental properties which may affect the function of the transistors so that the above described advantages of the low voltages necessary for control of the transistor remain. Especially the internal construction of the submicrometer transistor or nanotransistor can remain unchanged. Since the materials for the gate electrode can have metallic properties, there is also a capacitive connection between the detection electrode and the gate electrode as the control electrode of the transistor.

The gate oxide of a sensor according to the invention is comprised of a dielectric corresponding to the specifications of the nanotransistor.

BRIEF DESCRIPTION OF THE DRAWING

The invention is described in greater detail below with reference to several exemplary embodiments and the accompanying FIGURE whose sole FIGURE is a cross section of a sensor according to the invention based upon a field effect transistor. The dimensions the drawing are not shown to scale or as true dimensions.

SPECIFIC DESCRIPTION

Upon a silicon substrate 1 there is located a drain contact region 2, a source contact region 8 and a gate oxide 4 comprised of a dielectric like for example $SiO_2$ with a certain area. Substrate 1, drain contact area 2, source contact 8 and gate oxide 4 are comprised of materials which are known from the state of the art for submicrometer transistors and nanotransistors.

An especially configured gate electrode, according to the invention, comprises a region 6 with a contact area $A_{gate}$ for the contact oxide 4 and a region 5 with a contact area $A_{sens}$ for the detection electrode 7 and is disposed between gate oxide 4 and detection electrode 7. The contact area $A_{gate}$ is smaller than the contact area $A_{sens}$. An immobilized receptor 9 is provided on the region 5.

The channel below the gate oxide 4 has for example a length of only 0.01 micrometer. With these dimensions, a very small sensor area between the gate electrode material and the silicon substrate results. The contact area $A_{sens}$ with the detection electrode 7 can, for example have a length of 1 to 1000 micrometers. The contact area $A_{gate}$ at the gate oxide 4 can thus amount to for example $10^{-3}$ micrometer. Thus there is an increase in the charge density by a factor of 500,000. It will be self-understood that the surfaces are not limited to the dimensions given.

The gate electrode is configured with a T-shape in cross section in the present case. However, one is not limited in the choice of shape to the T-configuration. Rather any configuration can be selected for the gate electrode which can give rise ultimately to a greater area contact $A_{sens}$ at the detection electrode 7 by comparison with the contact area $A_{gate}$ at the gate oxide 4.

The material of the gate electrode 5, 6 is comprised of polysilicon. On the gate electrode there is found in the region 5 of the detection electrode 7, a further layer not illustrated in FIG. 1 of tungsten silicide as the surface of the gate electrode. On this the detection electrode 7 of silicon dioxide is disposed. Tungsten silicide is a very good conductor and advantageously prevents an ion flow from the detection electrode 7 to the gate oxide 4. The life of the transition is thereby increased. This function can also be assumed by a layer of titanium silicide.

The entire arrangement of drain contact region 2, source contact region 8 and gate electrode and detection electrode 7 is embedded in an insulator 3, for example in a silicon dioxide layer. This serves to protect the sensor. Instead, $Si_3N_4$ can also be used for this purpose.

The result is an arrangement in which there is a series circuit of two condensers. Because of the dimensioning there is an increase in the charge density in the direction of the transistor and thus the desired enhanced detection sensitivity of the transistor.

On the detection electrode 7 in the present case a nucleic acid (RNA, DNA) is preferably covalently or also electrostatically immobilized. When the analyte (here: a nucleic acid complementary to the immobilized nucleic acid RNA, DNA) is bound, the charge at the surface of the detection electrode is altered because of the additional bound negative charges of the phosphate groups of the analyte nucleic acid. Because of the series circuit of the condensers, this charge is transferred to the transistor. The resulting current change at the transistor is measured and can quantitatively be converted into the concentration of bound analyte and there is also qualitatively a simple detection of the analyte as well.

A replication of the DNA, RNA is no longer required in the case of a nanoresistor.

Following this principle, an antibody-antigen is also detectable or measurable.

In addition, an enzyme, for example a dehydrogenase or a glucose-oxidase in combination with a horse radish peroxidase can be immobilized on, for example, $Ta_2O_5$ as the detection electrode 7. Through the enzymatic reaction, the substrate is reacted which can protonate or deprotonate the surface of the detection electrode locally depending upon the pH value. The charge change is transmitted through the series circuit of the condensers and can produce a current change as described which can be measured. Based upon this system, conversion of all kinds of enzymes can be detected or measured in which the reaction mechanism gives rise to a local charge in the pH value at the surface of the detection electrode 7. It is also possible to immobilize various receptors on a detection electrode 7 in order to detect a plurality of analytes with a single sensor.

The invention claimed is:

1. A sensor for the detection of an analyte, the sensor comprising
    a substrate forming a first plate of a first capacitor,
    a source contact region on the substrate,
    a drain contact region on the substrate,
    a gate oxide of a transistor on the substrate between the source contact region and the drain contact region and forming an insulator of the first capacitor,
    a gate electrode having inner and outer faces, the inner face being smaller than the outer face and forming a second plate of the first capacitor, the outer face forming a first plate of a second capacitor connected in series with the first capacitor, the gate-electrode inner face contacting the gate oxide over a predetermined inner contact area;
    an electrically insulating detection electrode forming an insulator of the second capacitor and having inner and outer faces, the detection-electrode inner face contacting the gate-electrode outer face;
    an immobilized receptor fixed on the detection-electrode outer face for detecting a presence of the analyte and forming a second plate of the second capacitor; and
    an insulator body potting all of the source contact region, drain contact region, gate electrode, and gate oxide and the detection electrode except at the detection-electrode outer face carrying the immobilized receptor to form a series circuit of the two capacitors and increase a charge density toward the transistor to enhance a detection sensitivity of the transistor.

2. The sensor defined in claim 1 wherein a ratio of the contact areas amounts to 1:10 to 1:500,000.

3. The sensor defined in claim 1 wherein the detection electrode is made of $SiO_2$.

4. The sensor defined in claim 1 wherein the detection electrode is made of $Ta_2O_5$ or $Al_2O_3$ or $Si_3N_4$.

5. The sensor defined in claim 1 wherein the gate electrode contains polysilicon.

6. The sensor defined in claim 1 wherein the gate-electrode inner face has a silicide layer.

7. The sensor defined in claim 6 wherein the silicide layer is made of tungsten silicide or titanium silicide.

8. The sensor defined in claim 1 wherein the gate electrode is made of polysilicon and tungsten silicide and the detection electrode is made of silicon dioxide.

9. The sensor defined in claim 1 wherein the gate electrode is configured with a T-shape in cross section.

10. The sensor defined in claim 1 wherein the second capacitor is of greater capacitance than the first capacitor.

* * * * *